(12) United States Patent
Okoniewski (10) Patent No.: US 8,727,973 B2
(45) Date of Patent: May 20, 2014

(54) SEAL PORT WITH ADJUSTABLE HEIGHT

(75) Inventor: Gregory Okoniewski, North Haven, CT (US)

(73) Assignee: Covidien LP, Mansfield, MA (US)

(*) Notice: Subject to any disclaimer, the term of this patent is extended or adjusted under 35 U.S.C. 154(b) by 37 days.

(21) Appl. No.: 13/221,062

(22) Filed: Aug. 30, 2011

(65) Prior Publication Data
US 2012/0130187 A1 May 24, 2012

Related U.S. Application Data

(60) Provisional application No. 61/416,541, filed on Nov. 23, 2010.

(51) Int. Cl.
*A61B 1/32* (2006.01)

(52) U.S. Cl.
USPC ............................ 600/208; 600/206; 600/215

(58) Field of Classification Search
USPC ................. 600/201–249, 101, 104, 114, 184; 604/96.01, 104–109, 164.01, 523; 606/191–198, 1; 128/888
See application file for complete search history.

(56) References Cited

U.S. PATENT DOCUMENTS

| | | | |
|---|---|---|---|
| 5,514,133 A | 5/1996 | Golub et al. | |
| 5,524,644 A * | 6/1996 | Crook | 128/888 |
| 5,803,921 A | 9/1998 | Bonadio | |
| 5,906,577 A * | 5/1999 | Beane et al. | 600/207 |
| 6,033,426 A * | 3/2000 | Kaji | 606/213 |
| 6,958,037 B2 * | 10/2005 | Ewers et al. | 600/208 |
| 7,153,261 B2 | 12/2006 | Wenchell | |
| 7,758,500 B2 | 7/2010 | Boyd et al. | |
| 8,021,296 B2 | 9/2011 | Bonadio et al. | |
| 2002/0038077 A1 * | 3/2002 | de la Torre et al. | 600/203 |
| 2005/0192483 A1 * | 9/2005 | Bonadio et al. | 600/208 |
| 2005/0209608 A1 | 9/2005 | O'Heeron | |
| 2007/0203398 A1 | 8/2007 | Bonadio et al. | |
| 2008/0255519 A1 | 10/2008 | Piskun et al. | |
| 2010/0081880 A1 * | 4/2010 | Widenhouse et al. | 600/201 |
| 2011/0082341 A1 * | 4/2011 | Kleyman et al. | 600/206 |

(Continued)

FOREIGN PATENT DOCUMENTS

| | | | |
|---|---|---|---|
| EP | 0630660 A1 | 12/1994 | |
| EP | 0807416 A2 | 11/1997 | |

(Continued)

OTHER PUBLICATIONS

U.S. Appl. No. 13/091,246, filed Apr. 21, 2011, Paul D. Richard.

(Continued)

*Primary Examiner* — Todd Manahan
*Assistant Examiner* — Marcela I Shirsat (57) ABSTRACT

A surgical apparatus, for positioning within a tissue tract to access an underlying body cavity, is provided. The surgical apparatus includes a first and second member. The first member has a proximal ramp section, an accordion section, and a retaining portion. The first member defines a first longitudinal axis, a first proximal end, and a first distal end. The second member has a tubular proximal section, a portal portion, and a distal flange. The second member defines a second longitudinal axis, a second proximal end, and a second distal end. The second member includes a retaining structure to couple the first member to the second member. The first member is located at least partially in the tubular section of the second member.

14 Claims, 7 Drawing Sheets

(56) References Cited

U.S. PATENT DOCUMENTS

| | | | |
|---|---|---|---|
| 2011/0251463 A1 | 10/2011 | Kleyman | |
| 2011/0251464 A1 | 10/2011 | Kleyman | |
| 2011/0251465 A1 | 10/2011 | Kleyman | |
| 2011/0251466 A1 | 10/2011 | Kleyman | |
| 2012/0245430 A1* | 9/2012 | Kleyman et al. | 600/208 |
| 2013/0225933 A1* | 8/2013 | Kleyman | 600/208 |

FOREIGN PATENT DOCUMENTS

| | | |
|---|---|---|
| WO | WO96/10963 A1 | 4/1996 |
| WO | WO2005/058409 A1 | 6/2005 |
| WO | WO 2008/015566 A2 | 2/2008 |
| WO | WO2010/141409 A1 | 12/2010 |

OTHER PUBLICATIONS

U.S. Appl. No. 13/031,352, filed Feb. 21, 2011, Gennady Kleyman.
U.S. Appl. No. 13/193,647, filed Jul. 29, 2011, Russell Pribanic.
U.S. Appl. No. 13,217,717, filed Aug. 25, 2011, Joshua Stopek.
U.S. Appl. No. 13/221,062, filed Aug. 30, 2011, Gregory Okoniewski.
U.S. Appl. No. 13/223,029, filed Sep. 1, 2011, Michael Davis.
U.S. Appl. No. 13/223,330, filed Sep. 1, 2011, Gregory Okoniewski.
U.S. Appl. No. 13/223,336, filed Sep. 1, 2011, Michael Davis.
U.S. Appl. No. 13/223,613, filed Sep. 1, 2011, Greg Fischvogt.
U.S. Appl. No. 13/223,627, filed Sep. 1, 2011, Gregory Okoniewski.
U.S. Appl. No. 13/223,645, filed Sep. 1, 2011, Gennady Kleyman.
U.S. Appl. No. 13/223,659, filed Sep. 2, 2011, Francesco Alfieri.
U.S. Appl. No. 13/223,678, filed Sep. 1, 2011, Gregory Okoniewski.
U.S. Appl. No. 13/223,700, filed Sep. 1, 2011, Gennady Kleyman.
U.S. Appl. No. 13/224,353, filed Sep. 2, 2011, Gennady Kleyman.
U.S. Appl. No. 13/224,354, filed Sep. 2, 2011, Greg Okoniewski.
U.S. Appl. No. 13/224,355, filed Sep. 2, 2011, Anibal Rodrigues Jr.
U.S. Appl. No. 13/224,358, filed Sep. 2, 2011, Andrew Barnes.
U.S. Appl. No. 13/228,937, filed Sep. 9, 2011, Dino Kasvikis.
U.S. Appl. No. 13/228,960, filed Sep. 9, 2011, Russell Pribanic.
European Search Report EP08253236 dated Feb. 10, 2009.
European Search Report EP09251613 dated Mar. 24, 2011.
European Search Report EP10250526 dated Jun. 23, 2010.
European Search Report EP10250638 dated Jul. 19, 2010.
European Search Report EP10250643 dated Jun. 23, 2010.
European Search Report EP10250881 dated Aug. 18, 2010.
European Search Report EP10250885 dated Aug. 18, 2010.
European Search Report EP10250944 dated Jul. 29, 2010.
European Search Report EP10251218 dated Jun. 15, 2011.
European Search Report EP10251317 dated Oct. 15, 2011.
European Search Report EP10251359 dated Nov. 8, 2010.
European Search Report EP10251399 dated Sep. 13, 2010.
European Search Report EP10251486 dated Oct. 19, 2010.
European Search Report EP10251693 dated Feb. 3, 2011.
European Search Report EP10251718 dated Jan. 28, 2011.
European Search Report EP10251751 dated Apr. 28, 2011.
European Search Report EP10251796 dated Jan. 31, 2011.
European Search Report EP10251955 dated Feb. 21, 2011.
European Search Report EP10251983 dated Feb. 15, 2011.
European Search Report EP10251984 dated Feb. 10, 2011.
European Search Report EP10251985 dated Feb. 15, 2011.
European Search Report EP10251986 dated Mar. 7, 2011.
European Search Report for corresponding EP11250790 date of mailing is Jan. 25, 2012 (3 pgs).

* cited by examiner

SEAL PORT WITH ADJUSTABLE HEIGHT

CROSS REFERENCE TO RELATED APPLICATIONS

The present application claims the benefit of and priority to U.S. Provisional Patent Application Ser. No. 61/416,541 filed on Nov. 23, 2010, the entire contents of which are incorporated herein by reference.

BACKGROUND

1. Technical Field

The present disclosure relates generally to a surgical apparatus for positioning within a tissue tract accessing an underlying body cavity for use in minimally invasive surgical procedures, such as endoscopic and/or laparoscopic procedures, and more particularly, relates to a seal anchor member providing multiple instrument access through a single incision.

2. Description of Related Art

Increasingly, many surgical procedures are performed through small incisions in the skin. As compared to the larger incisions typically required in traditional procedures, smaller incisions result in less trauma to the patient. By reducing the trauma to the patient, the time required for recovery is also reduced. Generally, the surgical procedures that are performed through small incisions in the skin are referred to as "endoscopic". If the procedure is performed on the patient's abdomen, the procedure is referred to as "laparoscopic". Throughout the present disclosure, the term "minimally invasive" is to be understood as encompassing both endoscopic and laparoscopic procedures.

During a typical minimally invasive procedure, surgical objects, such as surgical access devices (e.g., trocar and cannula assemblies) or endoscopes, are inserted into the patient's body through the incision in tissue. In general, prior to the introduction of the surgical object into the patient's body, insufflation gas is used to enlarge the area surrounding the target surgical site to create a larger, more accessible work area. Accordingly, the maintenance of a substantially fluid-tight seal is desirable so as to inhibit the escape of the insufflation gas and the deflation or collapse of the enlarged surgical site.

To this end, various access devices with sealing features are used during the course of minimally invasive procedures to provide an access for surgical objects to enter the patient's body. However, a continuing need exists for an access port, which can position the access port with relative ease and with minor inconvenience for the surgeon.

SUMMARY

Disclosed herein is a surgical apparatus for positioning within a tissue tract to access an underlying body cavity including a first member and a second member. The first member has a proximal ramp section, an accordion section, and a retaining portion. The first member defines a first longitudinal axis, a first proximal end, and a first distal end. The second member has a tubular proximal section, a portal portion, and a distal flange. The second member defines a second longitudinal axis, a second proximal end, and a second distal end. The second member includes a retaining structure to couple the first member to the second member. The first member is located at least partially in the tubular section of the second member.

The first member has a proximal flange immediately adjacent to the proximal ramp section. The proximal ramp section is shaped to increase an outer diameter of the first member from the accordion section to the proximal flange. The accordion section of the first member includes a plurality of convolutions configured to be folded onto each other to decrease a longitudinal length of the first member. The retaining portion of the first member may be a distal flange extending radially along the distal end of the first member.

The second member is deformable. The second member is constructed of an elastic material. The second member is constructed of an open-cell polyurethane foam, a thermoplastic elastomer (TPE), a gel, or a polyisoprene material.

The surgical apparatus may include a drawstring attached to the second member and to a post extending proximally from the proximal flange of the first member.

The second member defines a concave recess extending proximally into the second member from the second distal end. The second member is molded onto the first member.

The portal portion includes at least one port adapted for the substantially sealed reception of an object, e.g., a surgical instrument, therein.

These and other features of the current disclosure will be explained in greater detail in the following detailed description of the various embodiments.

BRIEF DESCRIPTION OF THE DRAWINGS

Various embodiments of the present disclosure are described hereinbelow with reference to the drawings, wherein.

Other features of the present disclosure will become apparent from the following detailed description, taken in conjunction with the accompanying drawings, which illustrate, by way of example, the principles of the present disclosure.

DETAILED DESCRIPTION OF THE EMBODIMENTS

Particular embodiments of the present disclosure will be described herein with reference to the accompanying drawings. As shown in the drawings and as described throughout the following description, and as is traditional when referring to relative positioning on an object, the term 'proximal' or 'trailing' refers to the end of the apparatus that is closer to the user and the term 'distal' or 'leading' refers to the end of the apparatus that is further from the user. In the following description, well-known functions or constructions are not described in detail to avoid obscuring the present disclosure in unnecessary detail.

The present disclosure is for use in a minimally invasive procedure using one or more surgical instruments through a single access device. The disclosed procedure involves insufflating the body cavity and positioning a portal member within, e.g., the navel of the patient. In addition, while certain aspects of this disclosure are described as relating to laparoscopic surgery via the abdominal wall, it should be understood that the present invention is equally relevant to, and may be employed in connection with, other types of surgery such as incision-less surgery, whereby access to a body cavity is provided via a natural orifice such as the vagina, anus, mouth, ear, nasal passage, etc. Instruments including an endoscope and additional instruments such as graspers, staplers, forceps or the like may be introduced within the surgical portal to carry out the surgical procedure. The surgical portal in the procedure may be introduced into an incision (e.g., Hasson incision) with a Kelly clamp.

Figure 1:
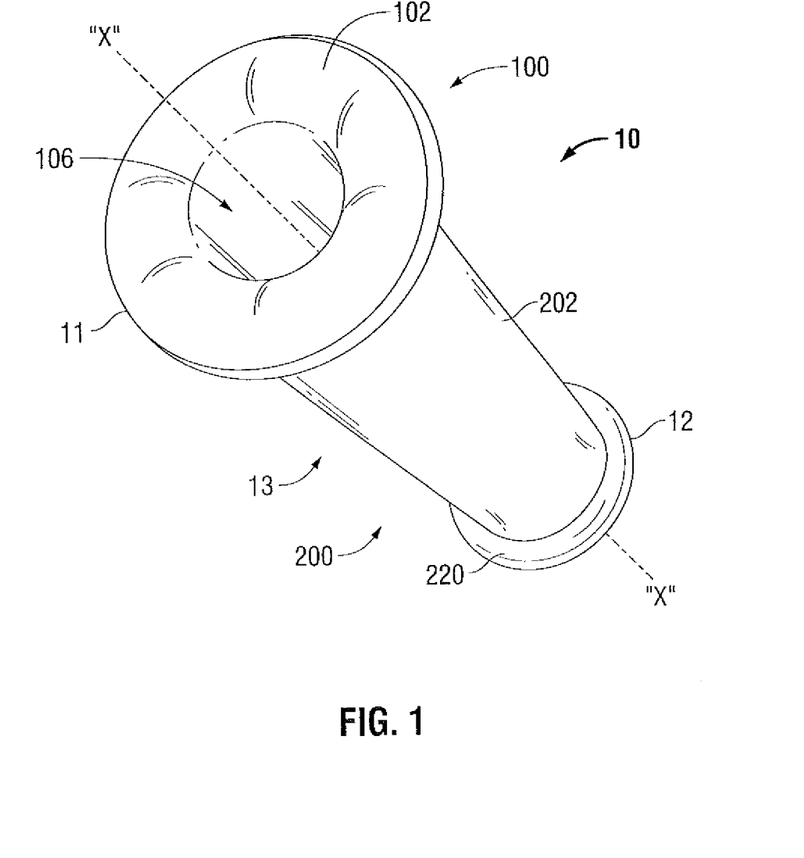
FIG. 1 is a perspective view of a surgical portal in accordance with the present disclosure.

Disclosed herein are surgical portals that are configured and adapted to transition among an expanded length, a contracted length, and intermediate lengths between the contracted and expanded lengths. The surgical portals may be configured and adapted to maintain a particular length selected by a user until the user readjusts the length. Referring now to the drawings, a first embodiment of a surgical portal in which like reference numerals identify identical or substantially similar parts throughout the several views, FIG. 1 illustrates a surgical portal 10 for use in, for example, the above-identified procedure. With reference to FIG. 1, the surgical portal 10 defines a trailing end 11 and a leading end 12. An axial dimension or length 'L1' is defined longitudinally along a fully extended intermediate section between trailing and leading ends 11, 12.

Disposed between the trailing end 11 and the leading end 12 is an intermediate section 13. The cross-section of intermediate section 13 may exhibit any suitable configuration, e.g., substantially circular, oval, oblong, or non-circular. The trailing end 11 is shaped to rest on the outer surface of a patient (e.g., skin) and to keep the clamping member 100 from fully entering the body cavity.

Figure 4:
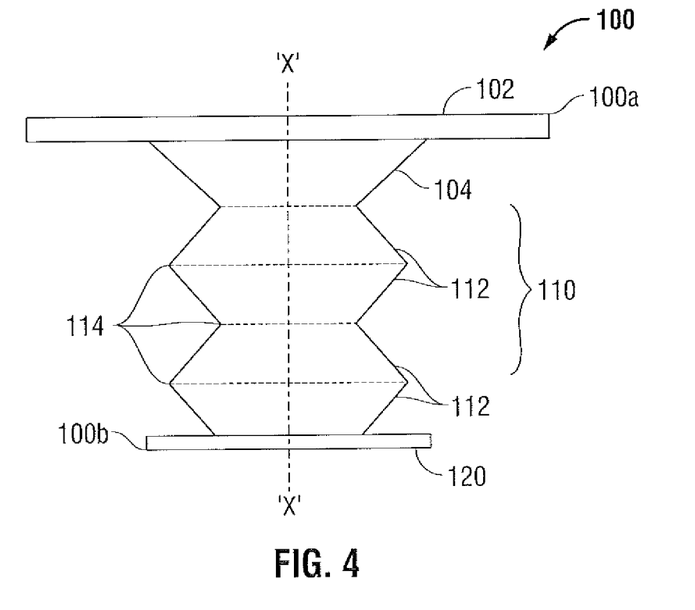
FIG. 4 is a cross-sectional side view of a clamping member of FIGS. 1-3.

The surgical portal 10 includes a clamping member 100 and a seal anchor member 200. With reference to FIG. 4, the clamping member 100 includes a proximal flange 102 and an accordion section 110 extending distally from the proximal flange 102. The proximal flange 102 extends radially outward from the accordion section 110. A longitudinal 'X' axis is defined as extending through the longitudinal center of the accordion section 110.

The accordion section 110 includes several convolutions 112. Each of the convolutions 112 are connected at a flexible hinge 114 with an adjacent convolution 112. The convolutions 112 are capable of folding on top of each other to decrease the overall length of the clamping member 100, or the convolutions 112 can be unfolded, to extend away from adjacent convolutions and to increase the overall length of the clamping member 100. The accordion section 110 may be transitioned to a variety of positions and are adapted to retain a particular position unless acted upon by a force.

Figure 2:
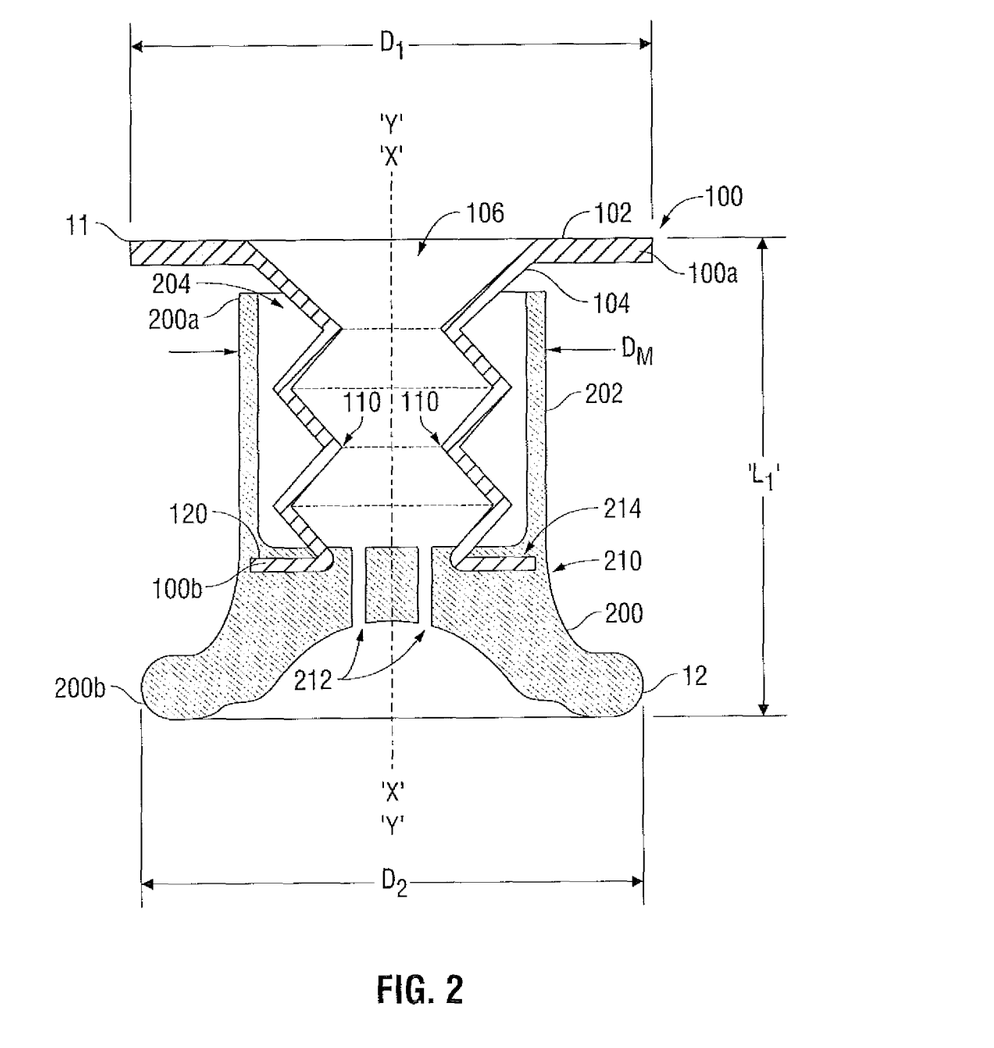
FIG. 2 is a cross-sectional side view of a surgical portal in accordance with the present disclosure, shown in a first or expanded condition.

With additional reference to FIG. 2, the clamping member 100 defines a ramp 104, a proximal end 100a, a distal end 100b, and a longitudinal passage 106 that has a funnel-shaped configuration to facilitate insertion of a surgical instrument (not shown) therethrough. The ramp 104 is located between and connects the accordion section 110 to the proximal flange 102. The ramp 104 acts to transition the accordion section 110, which has a relatively smaller outer diameter, into the proximal flange 102, which has a relatively larger outer diameter.

The clamping member 100 includes a retainer 120 located about the distal end 100b of the accordion section 110. As disclosed, the retainer 120 is a horizontal flange that extends radially outward from the accordion section 110. The retainer 120 is shaped and sized to mate with a retaining structure 214 of the seal anchor member 200. As disclosed in FIG. 5, the retaining structure 214 is a void in the seal anchor member 200. The retainer 120 and the retaining structure 214 couple the clamping member 100 together with the seal anchor member 200 to create a single portal unit.

It is well known in the art to join individual components into a single unit. Some examples of joining methods include co-molding the components and the use of adhesives. It is contemplated that these joining methods, as well as others known in the art, may be used to couple the clamping member 100 to the seal anchor member 200.

Figure 5:
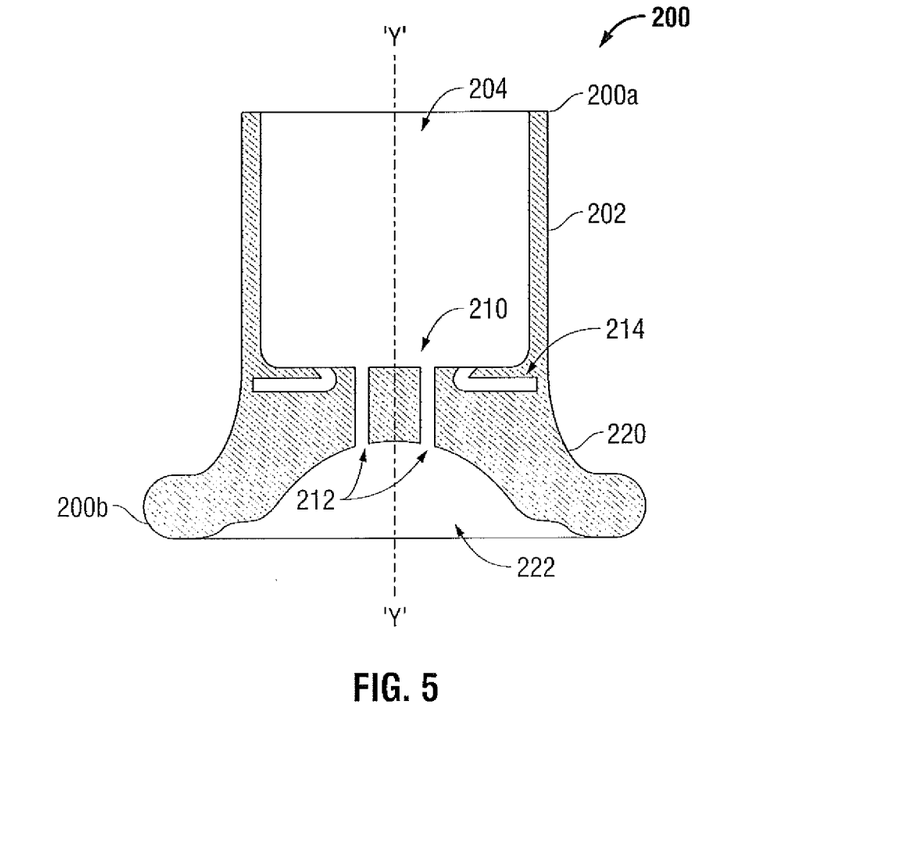
FIG. 5 is a cross-sectional side view of a seal anchor member of FIGS. 1-3.

With reference to FIG. 5, the seal anchor member 200 includes a tubular section 202 at the proximal end 200a, a portal portion 210 that extends distally from the tubular section 202, and a bulb or distal flange 220 that extends distally from the portal portion 210. The tubular section 202 defines an opening 204 and a longitudinal 'Y' axis that is co-axial with the longitudinal 'X' axis of the clamping member 100 when coupled together. The opening 204 is sized and shaped to accept the accordion section 100 therethrough.

The seal anchor member 200 defines one or more ports 212 that extend longitudinally along the portal portion 210. While the portal portion 210 is shown as having multiple ports 212, the portal portion 210 may in some embodiments have one or more longitudinally extending ports 212. The ports 212 extend along parallel to the axis 'Y' of the portal portion 210. The ports 212 are configured and adapted to receive a surgical object, including, e.g., minimally invasive grasper instruments, forceps, clip-appliers, staplers, etc.

Prior to the insertion of the surgical object, each port 212 is in a first state in which the port 212 defines a first or initial dimension. The port 212 may incorporate a slit extending the longitudinal length of the portal portion 210. The ports 212 are substantially closed in the absence of a surgical object inserted therein thereby inhibiting the escape of insufflation gas through the port 212 in the first state. Upon the introduction of a surgical object into the port 212, the port 212 transitions to a second state to substantially approximate the diameter of the surgical object, such that a substantially fluid-tight seal is formed therewith, thereby substantially inhibit the escape of insufflation gas through port 212.

The portal portion 210 may be formed from a semi-rigid material to facilitate a range of motion of the surgical object (not shown for clarity) inserted within the ports 212 of the portal portion 210.

Figure 6:
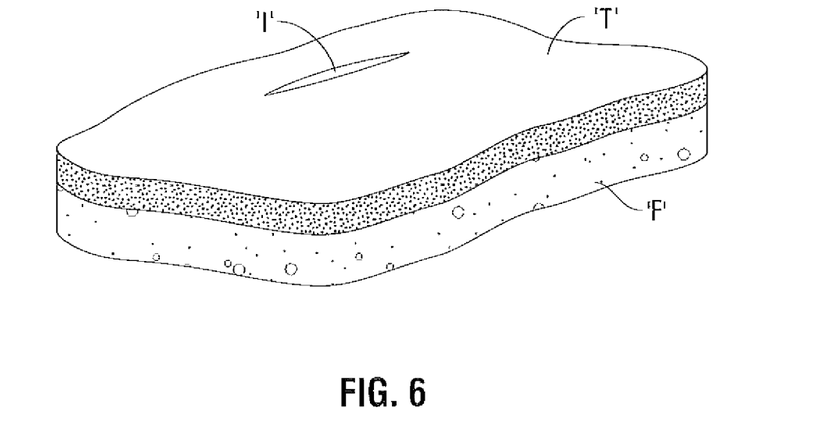
FIG. 6 is a perspective cross-sectional view of an incision made on a tissue layer at a surgical site.

The distal flange 220 defines a concave recess 222 extending from the distal end 200b inward to the portal portion 210. The distal flange 220 is substantially arcuate to assist in the insertion of seal anchor member 200 within an incision 'I' formed in tissue 'T', e.g., as discussed in further detail below and shown in FIG. 6.

With additional reference to FIG. 2, the trailing end 11 defines a first diameter $D_1$, and the leading end 12 defines a second diameter $D_2$. As disclosed, the respective first and second diameters $D_1$, $D_2$ are not equal. It is contemplated that the first and second diameters $D_1$, $D_2$ are substantially similar.

The intermediate section 13 defines a middle diameter $D_M$. The respective diameters $D_1$, $D_2$ of the trailing and leading ends 11, 12 are substantially larger than the middle diameter $D_M$ of the intermediate portion 13 thereby giving surgical portal 10 an 'hour-glass' configuration. Subsequent to insertion, the second diameter $D_2$ of the leading end 12 is also substantially larger than the dimension of the tissue incision 'I'. Consequently, removal of the surgical portal 10 from the tissue incision 'I' is hindered and thus, surgical portal 10 will remain anchored within the tissue 'T' until enough force is applied to pull the surgical portal 10 from the tissue incision 'I'.

Figure 3:
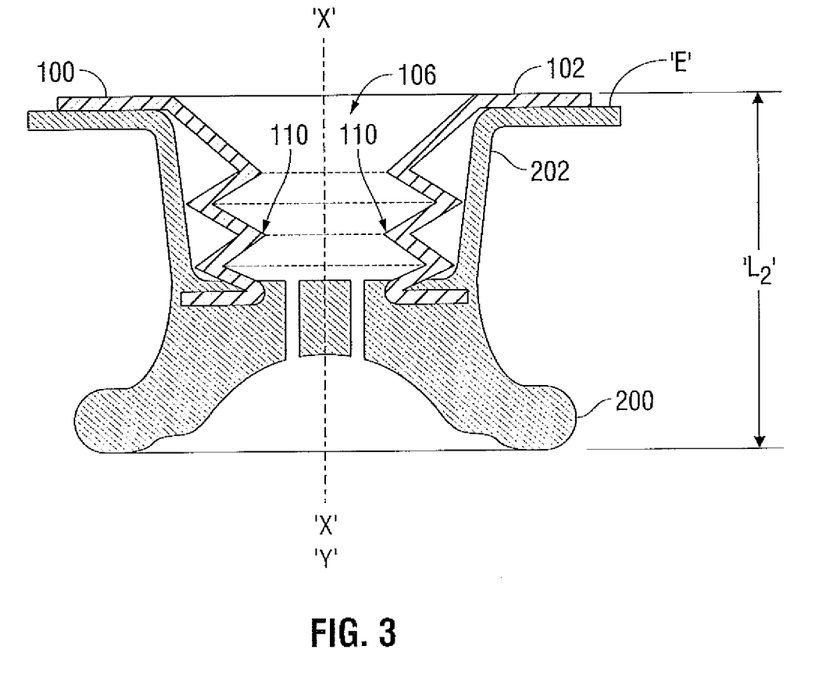
FIG. 3 is a cross-sectional side view of the surgical portal of FIGS. 1 and 2, shown in a second or collapsed condition.

The intermediate section 13 is configured and adapted to be angled with respect to a longitudinal 'X' axis of the seal anchor member 100 and/or to be expanded or contracted along longitudinal 'X' axis between a first length L1 (FIG. 2) and a second length L2 (FIG. 3). In particular, the intermediate section 13 may be rotated or bent at various angles with respect to the longitudinal 'X' axis by collapsing or expanding portions of the accordion section 110 for surgical objects that are non-straight, i.e., angled, or are bendable or pliable. Unless acted upon by a force, the intermediate section 13 retains the configuration in which it was set by the user. The ability of the intermediate section 13 to retain a set configuration is a property of the material used.

Figure 7:
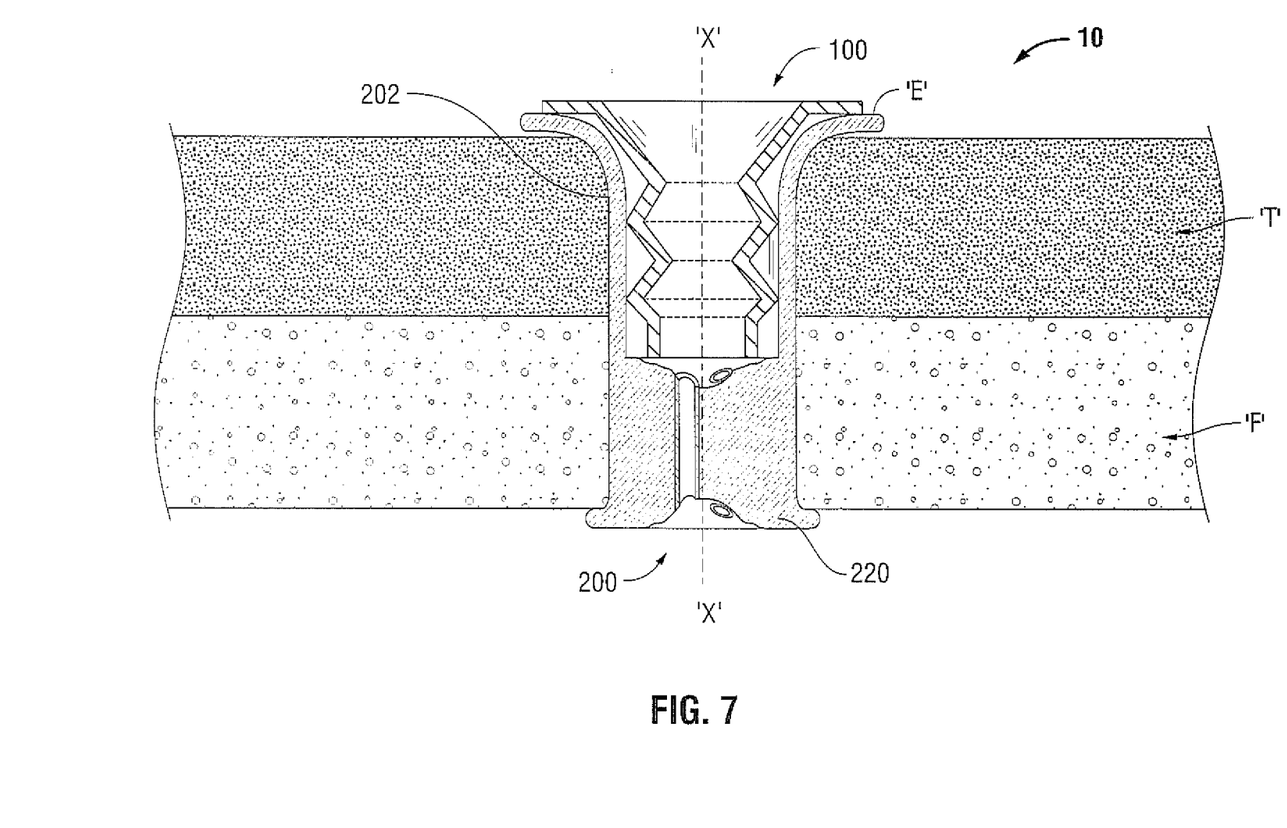
FIG. 7 is a cross-sectional side view of surgical portal in accordance with FIGS. 1-5, shown in a partially collapsed condition relative to a tissue.

With reference to FIGS. 2, 3, and 7, clamping member 100 may be formed from a semi-rigid biocompatible material that allows the folding and unfolding of the accordion section 110, which in turn translates the proximal flange 102 with respect to the seal anchor member 200 along the longitudinal 'X' axis.

The translation of the proximal flange 102 distally into the tubular member 202 causes a part of the tubular member 202 to roll outward away from the longitudinal 'X' axis. The tubular section 202 adjacent to the proximal flange 102 acts to seal the proximal flange 102 against the tissue 'T'. The excess tubular section 'E', i.e., the tubular section 202 that extends beyond the proximal flange 102, may be trimmed.

The seal anchor member 200 is formed of a flowable or sufficiently pliable material, such as a foam material, e.g., an open-cell polyurethane foam, a thermoplastic elastomer (TPE) or a gel. The formation of a seal anchor member 200 may involve a process whereby an inert gas, such as carbon dioxide or nitrogen is infused into the material so as to form a foam structure. Seal anchor member 200 may also be coated with a lubricious coating, e.g., Parylene N or C, to ease insertion of instruments and/or cannula therethrough.

Portal portion 210 may be made from a disposable, compressible, and/or flexible type material, for example, but not limited to, a suitable foam or gel material having sufficient compliance to form a seal about one or more surgical objects and also establish a sealing relation with the tissue. The foam is preferably sufficiently compliant to accommodate off axis motion of the surgical object. In one embodiment, the foam includes a polyisoprene material. Suitable portal members are disclosed in commonly assigned U.S. Patent Application Publication No. 2009/0093752, which was filed on Oct. 2, 2008, the entire contents of which is hereby incorporated by reference herein.

Figure 8:
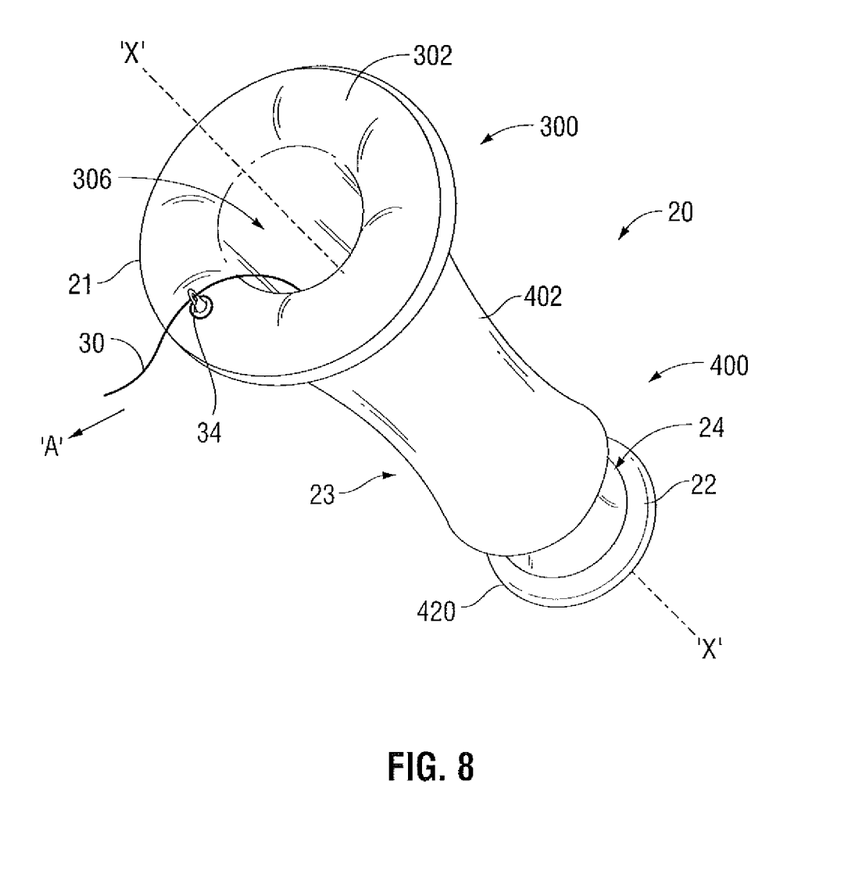
FIG. 8 is a perspective view of another embodiment of a surgical portal in accordance with the present disclosure.
Figure 9:
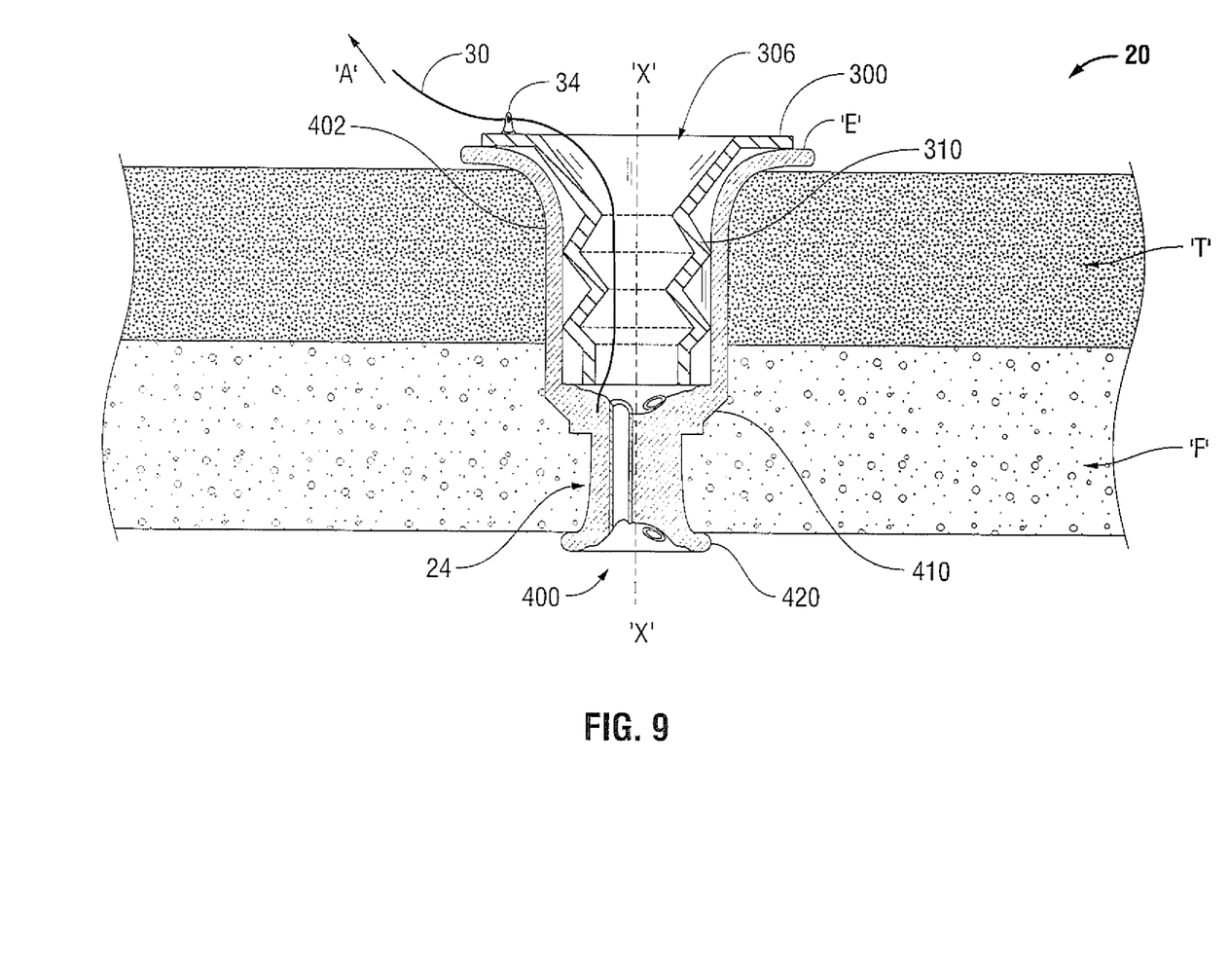
FIG. 9 is a perspective view of surgical portal in accordance with FIG. 8, shown in a partially collapsed condition relative to a tissue.

In another embodiment, a surgical portal 20, shown in FIGS. 8 and 9, includes a drawstring 30 connected with the portal portion 410. The drawstring 30 passes through the longitudinal passageway 306 of the clamping member 300 and connects with a post 34 on the proximal flange 302 of the clamping member 300. It is envisioned that more than one drawstring 30 and post 34 is incorporated into the surgical portal 20.

By pulling the drawstring 30 through the longitudinal passageway 306, the surgical portal 20 transitions from the first state having an expanded length L1 (FIG. 2) to the second state having a contracted length L2, as discussed in regard to surgical portal 20.

Upon achieving the desired overall length of the surgical portal 20, the drawstring is secured about the post 34, such that the length of the surgical portal 20 is maintained. As discussed above, pulling the drawstring 30 will adjust the overall height of the surgical portal 20. In particular, the surgeon may adjust the overall height by pulling on the drawstring 30 in the direction indicated by arrow 'A', while pressing on the proximal flange 302 to ensure that the proximal flange 302 does not move with the drawstring 30, thereby collapsing the longitudinal passageway 306. In so doing, the length of drawstring 30 between the portal portion 410 and the proximal flange 302 will be decreased. In the collapsed state, the distal flange 420 is set against an inner layer of tissue 'F' to seal the surgical portal 20 against the inner layer of tissue 'F', and the tubular section 402 is flared out and is trapped between the clamping member 300 and the outer layer of tissue 'T' to seal the surgical portal 20 against the outer layer of tissue 'T'.

The surgical portal 20 includes a trailing end 21 and a leading end 22. Disposed between the trailing end 21 and the leading end 22 is an intermediate section 23 having a recessed section 24. Seal anchor member 400 defines a cross-sectional dimension that varies along length 'L', as such, the seal anchor member 400 has an hour-glass configuration, which facilitates the anchoring of seal anchor member 400 within tissue 'T'.

In other embodiments and as is well known in the art, the drawstring 30 may form part of a ratchet-type mechanism (not shown for clarity), which allows the drawstring 30 to be drawn in a first direction and optionally inhibits the drawstring 30 from being translated in the opposite direction. The ratchet-type mechanism may be disengaged and the accordion sections 310 will expand to their biased conditions such that the surgical portal 20 will transition toward the first expanded length L1.

In an embodiment, the accordion sections 310 may be spring-loaded and may be biased to an expanded condition.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical apparatus for positioning within a tissue tract to access an underlying body cavity, the surgical apparatus comprising:
    a first member defining a proximal ramp section, an accordion section, a retaining portion, and a longitudinal passage, the retaining portion located at a distal end of the first member; and
    a second member defining a tubular section, a portal portion, and a distal flange, the second member having a plurality of ports defined by the portal portion;
    the second member including a retaining structure located in a distal portion of the second member to couple the first member to the second member;
    the first member being located at least partially in the tubular section of the second member, the longitudinal passage defined by the first member providing access to the plurality of ports defined by the portal portion of the second member, wherein the surgical apparatus is translatable between a first position where the second member has a first length and a second position where the second member has a second length different from the first length.

2. The surgical apparatus of claim 1, wherein the first member has a proximal flange immediately adjacent to the proximal ramp section, the proximal ramp section being configured to increase an outer diameter of the first member from the accordion section to the proximal flange.

3. The surgical apparatus of claim 2, wherein the surgical apparatus further includes a drawstring attached to the portal portion of the second member and to a post extending proximally from the proximal flange of the first member.

4. The surgical apparatus of claim 3, wherein the drawstring is configured to translate the surgical apparatus between the first position and the second position.

5. The surgical apparatus of claim 1, wherein the second member is deformable.

6. The surgical apparatus of claim 5, wherein the second member is constructed of an elastic material.

7. The surgical apparatus of claim 5, wherein the second member is constructed of a material selected from the group consisting of an open-cell polyurethane foam, a thermoplastic elastomer (TPE), a gel, and a polyisoprene material.

8. The surgical apparatus of claim 5, wherein the second member defines a concave recess extending proximally into the second member.

9. The surgical apparatus of claim 1, wherein the accordion section of the first member includes a plurality of convolutions configured to be folded onto each other to decrease a longitudinal length of the first member.

10. The surgical apparatus of claim 1, wherein the retaining portion of the first member is a distal flange extending radially along the distal end of the first member.

11. The surgical apparatus of claim 1, wherein the second member is molded with the first member.

12. The surgical apparatus of claim 1, wherein at least one of the plurality of ports is adapted for the substantially sealed reception of a surgical object therein.

13. The surgical apparatus of claim 1, wherein the accordion section of the first member is located at least partially in the tubular section of the second member.

14. The surgical apparatus of claim 1, wherein translating the surgical apparatus from the first position to the second position causes the tubular proximal section to roll outward.

* * * * *